United States Patent
Piao et al.

(10) Patent No.: US 7,018,645 B1
(45) Date of Patent: Mar. 28, 2006

(54) MIXTURES OF VARIOUS TRIBLOCK POLYESTER POLYETHYLENE GLYCOL COPOLYMERS HAVING IMPROVED GEL PROPERTIES

(75) Inventors: Ai-Zhi Piao, Salt Lake City, UT (US); Chung Shih, Sandy, UT (US)

(73) Assignee: Macromed, Inc., Sandy, UT (US)

(*) Notice: Subject to any disclaimer, the term of this patent is extended or adjusted under 35 U.S.C. 154(b) by 0 days.

(21) Appl. No.: 09/559,799

(22) Filed: Apr. 27, 2000

(51) Int. Cl.
 *A61F 2/00* (2006.01)
 *A61F 13/00* (2006.01)
 *A61K 9/48* (2006.01)
 *A61K 9/20* (2006.01)
 *A61K 9/22* (2006.01)

(52) U.S. Cl. ............ 424/426; 424/428; 424/430; 424/434; 424/443; 424/449; 424/451; 424/457; 424/468; 424/484; 424/486; 424/464; 604/891.1

(58) Field of Classification Search ......... 424/400, 424/422, 423, 426, 428, 443, 444, 484, 486, 424/425, 424; 514/964; 604/891.1, 892.1; 523/122
See application file for complete search history.

(56) References Cited

U.S. PATENT DOCUMENTS

| 4,438,253 A | 3/1984 | Casey et al. |
| 4,526,938 A | 7/1985 | Churchill et al. |
| 4,652,441 A | 3/1987 | Okada et al. |

(Continued)

FOREIGN PATENT DOCUMENTS

| EP | 0 092 918 | 3/1983 |
| EP | 0 258 780 | 8/1987 |
| EP | 0092918 B1 * | 10/1988 |
| WO | GB93/01079 | 5/1992 |

OTHER PUBLICATIONS

Byeongmoon Jeong, et al, "Biodegradable Block Copolymers as Injectable Drug–delivery Systems", *Letters to Nature*, vol. 388, Aug. 28, 1997, p. 860, line 5–9.

A Chenite, et al, "Novel Injectable Neutral Solutions of Chitosan Form Biodegradable Gels In Situ", *Biomaterials*, 21 (2000) 2155–2161, p. 2155, col. 1, lines 5–7.

E. Ruel–Gariepy, et al, "Thermosensitive Chitosan–based Hydrogel Containing Liposomes for the Delivery of Hydrophilic Molecules", *Journal of Controlled Release*, 82 (2002) 373–383, p. 374, column 1, lines 32–36.

AS Sawhney and JA Hubbell, Rapidly Degraded Terpolymers of dl–Lactide, Glycolide, and εCaprolactone with Increased Hydrophilicty by Copolymerization with Polyethers, *J. Biomed. Mat. Res.*,24, 1397–1411(1990).

(Continued)

*Primary Examiner*—Michael G. Hartley
*Assistant Examiner*—Sharmila S. Gollamudi
(74) *Attorney, Agent, or Firm*—Thorpe North & Western, LLP (57) ABSTRACT

A water soluble, biodegradable reverse thermal gelation system comprising a mixture of at least two types of tri-block copolymer components is disclosed. The tri-block copolymer components are made of a hydrophobic biodegradable polyester A-polymer block and a hydrophilic polyethylene glycol B-polymer block. The drug release and gel matrix erosion rates of the biodegradable reverse thermal gelation system may be modulated by various parameters such as the hydrophobic/hydrophilic component contents, polymer block concentrations, molecular weights and gelation temperatures, and weight ratios of the tri-block copolymer components in the mixture.

12 Claims, 4 Drawing Sheets

U.S. PATENT DOCUMENTS

| | | | |
|---|---|---|---|
| 4,745,160 A | | 5/1988 | Churchill et al. |
| 4,892,903 A | * | 1/1990 | Himes .................... 524/488 |
| 4,938,763 A | | 7/1990 | Dunn et al. |
| 5,100,669 A | | 3/1992 | Hyon et al. |
| 5,278,202 A | | 1/1994 | Dunn et al. |
| 5,324,519 A | | 6/1994 | Dunn et al. |
| 5,330,768 A | | 7/1994 | Park et al. |
| 5,674,192 A | * | 10/1997 | Sahatjian et al. ............. 604/28 |
| 5,702,217 A | | 12/1997 | Cha |
| 5,702,717 A | * | 12/1997 | Cha et al. .................. 424/425 |
| 5,939,485 A | * | 8/1999 | Bromberg et al. .......... 524/556 |
| 6,004,573 A | * | 12/1999 | Rathi et al. ................. 424/426 |
| 6,117,949 A | * | 9/2000 | Rathi et al. ................. 525/415 |

OTHER PUBLICATIONS

AS Sawhney, CP Pathak, and JA Hubell, Bioeroedible Hydrogels Based on Photopolymerized Poly(ethylene glycol)–c9–poly(α–hydroxy acid) Diacrylate Macromers, *Macromolecules*, 26(4). 581–589: 1993.

T Matsuda, N Motomura, and T Oka, Angiopeptin as a Potent Inhibitor of Myointimal Hyperplasia: Systemic Injection and Local Administration via Impregnation in a Biodegrable Polymeric Gel, *ASAIO Journal*, M512–M517(1993).

L Martini et al., Micellisation and Gelation of Triblock Copolymer of Ethylene Oxide and ε–Caprolactone, CLE, CL in Aqueous Solution, *J. Chem Soc. Faraday Trans.*, 90(13), 1961–1966: 1994.

TP Johnston and SC Miller, Inulin Diposition Following Intramuscular Administration of an Inulin/Poloxamer Gel Matrix, *J. Parenteral Science & Technology*, 43(6), Nov.–Dec. 1989.

TP Johnston et al., Sustained Delivery of Interleukin–2 from a Poloxamer 407 Gel Matrix Following Intraperitoneal Injection in Mice, *Pharmaceutical Research* 9(3), 1992.

K, Morikawa et al., Enhancement of Therapeutic Effects of Recombinant Interleukin 2 on a Transplatantable Rat Fibrosarcoma by the Use of a Sustained Release Vehicle, Pluronic Gel, *Cancer Tesearch*, 47 pp. 37–41, Jan. 1, 1987.

TP Johnson and SC Miller, Toxicological Evaluation of Poloxamer Vehicle4s for Intramuscular Use, *J. Parenteral Science and Technology*, 39(2), Mar.–Apr. 1985.

L. Youxin, C Volland, and T Kissel, In–Vitro Degradation and Bovine Serum Albumin Release of the ABA Triblock Copolymers Consisting of poly (L(+)lacric acid–co–glycolic acid) A–Blocks attached to Central Polyoxyethylene B–Blocks, *J. Controlled Release*, 32: 1994.EXAMINER.

L. Youxin and T Kissel, Synthesis and Properties of Biodegradable ABA Triblock Copolymers Consisting of poly(L–lacric acid) or poly(L–lacric–co–glycolic acid) A–Blocks attached to Central Poly(oxyethylene) B–Blocks, *J. Controlled Release*, 27; 1993.

KA Fults and TP Johnston, Sustained–Release of Urease from a Poloxamer Gel Matric, *J. Parenteral Science & Technology*, 44(2), Mar.–Apr. 1990.

* cited by examiner

MIXTURES OF VARIOUS TRIBLOCK POLYESTER POLYETHYLENE GLYCOL COPOLYMERS HAVING IMPROVED GEL PROPERTIES

The present invention relates to water soluble mixtures of two or more types of biodegradable block copolymers and their use in parenteral, ocular, transdermal, vaginal, buccal, transmucosal, pulmonary, transurethral, rectal, nasal, oral, or aural administration of drugs. More particularly, this invention relates to compositions having improved reverse thermal gelation properties comprising two or more biodegradable triblock copolymers consisting of biodegradable polyester and polyethylene glycol (PEG) blocks.

BACKGROUND OF THE INVENTION AND SUMMARY OF PRIOR ART

Many biologically active macro-molecules, such as peptides/proteins and DNA, that are effective for gene therapy and a variety of therapeutic applications, have become commercially available through advances in recombinant DNA and other technologies. However, these molecules,are limited to parenteral administration due to their susceptibility to degradation in the gastrointestinal tract. Treatment for chronic illnesses or indications may require multiple injections per day over many days, or months. Patient compliance is usually poor. Therefore, it would be highly desirable to develop a system for the delivery of bioactive agents or drugs, in particular, polypeptide or protein drugs, at a controlled rate over a sustained period of time without the above mentioned problems. This system would help to optimize the therapeutic efficacy, minimize the side effects, and thereby improve patient compliance.

Drug loaded polymeric devices and dosage forms have been investigated for long term therapeutic treatment of different diseases. Because of strict regulatory compliance requirements such as biocompatibility, having a clearly defined degradation pathway, and safety of the degradation products, there are currently few synthetic or natural polymeric materials which can be used for the controlled delivery of drugs, including peptide and protein drugs.

In copending U.S. application Ser. No. 09/396,589, filed Sep. 15, 1999 which is a continuation in-part of U.S. application Ser. No. 09/164,865 filed Oct. 1, 1998 which in turn is a continuation-in-part of U.S. Pat. No. 6,004,573 which was filed on Oct. 3, 1997 and issued Dec. 21, 1999, there is disclosed a biodegradable reverse thermal gelation system comprising ABA- or BAB-type block copolymers having an average molecular weight of between about 2000 and 4990 consisting of about 51 to 83% by weight of a hydrophobic A polymer block comprising a biodegradable polyester, and about 17 to 49% by weight of a hydrophilic B polymer block consisting of polyethylene glycol (PEG). It is surprising that a block copolymer with such a large proportion of hydrophobic component would be water soluble below normal room temperatures, such as temperatures as low as 5° C.

The reverse thermal gelation system referenced in the preceding paragraph causes minimal toxicity and minimal mechanical irritation to the surrounding tissue because of the biocompatibility of the materials and pliability of the gel. In addition, these block copolymers biodegrade into non-toxic units. The drug release, gel strength, gelation temperature and degradation rate of each reverse gelation system can be controlled by proper design and preparation of the various copolymer blocks, namely, through modifications of the weight percent of A-blocks and B-blocks, the mole percentages of lactate and glycolate moieties making up the A-blocks, and the molecular weight and polydispersity of the ABA or BAB triblock copolymers. Drug release is also controllable through adjustment of the concentration of the block copolymer in the drug delivery liquid. It would be desirable to provide a biodegradable reverse gelation system having a gelation temperature within a desired range so that the system remains as a liquid at an ambient temperature, but become a gel at the body temperature of the object to which the drug is delivered. A reverse thermal gelation system with such gelation temperatures can be processed, formulated and dispensed at ambient temperatures, thereby significantly reducing manufacturing and handling costs. In addition, accidental gelation during application, e.g. gelation in the syringe during injection can be avoided. As discussed above, the gelation temperature of a reverse thermal gelation system may be modified by changing the chain length, the glycolide/lactide (G/L) mole ratio of the A-polymer block, the molecular weight of the B-polymer block, the weight ratio of A block and B block polymers, and by various additives. However, the above modifications also change the gel qualification as well as the gelation temperature. In addition, some additives may not be compatible with the drug to be delivered. Therefore, it is desirable to provide a reverse gelation system with adjustable gelation temperatures without changing its desirable gel qualities significantly.

It has been discovered that mixtures or blends of two or more tri-block polyester/polyethylene glycol(PEG) copolymers provides for improved reverse thermal gelation properties, such as an optimum gelation temperature, gel strength, degradation rate, and yet still maintains the desirable gel qualities. In addition, a combination of two or more different tri-block polyester/polyethylene glycol copolymers increases design flexibility. Such drug delivery systems have properties such as modulated drug release and modulated matrix erosion. These mixtures or blends of tri-block polyester\polyethylene glycol copolymers are very useful in drug delivery practice because they allow optimization to fit individual drug or patient's needs. Therefore, the present invention provides for a significant improvement in the art.

OBJECTS AND SUMMARY OF THE INVENTION

It is an object of the present invention to provide drug delivery systems that are biodegradable, exhibit improved reverse thermal gelation behavior, and provide improved drug release characteristics.

A further object of this invention is to provide a drug delivery system for the parenteral administration of hydrophilic or hydrophobic drugs, peptide or protein drugs, hormones, genes, oligonucleotides or anti-cancer agents.

Another object of this invention is to provide a method for the parenteral administration of drugs in a biodegradable polymeric matrix which results in the formation of a gel depot within the body from which the drugs are released at a controlled rate.

These and other objects are accomplished by providing a biodegradable copolymer composition having improved reverse thermal gelation properties, said composition comprising a mixture or blend of at least two types of biodegradable polyester(A-block)/polyethylene glycol(B-block) ABA or BAB tri-block copolymer components in a proper ratio so that the mixture has the desired reverse thermal gelation properties. One component (Component I) of the triblock copolymer mixture has an average molecular weight of between about 2500 and about 8000, preferably 3000 to 6500, and consists of a biodegradable polyester A-polymer block and a polyethylene glycol (PEG) B-polymer block in a ratio by weight of 1.3 to 3.0, preferably 1.8 to 2.6. The other component (Component II) of the triblock copolymer has an average molecular weight of between about 800 and about 7200, preferably 1500 to 6000, and consists of a biodegradable polyester A-polymer block and a polyethylene glycol (PEG) B-polymer block in a ratio by weight of 0.37 to 2.6, preferably 0.54 to 2.5.

Preferably, the biodegradable polyester is synthesized from monomers selected from the group consisting of D,L-lactide, D-lactide, L-lactide, D,L-lactic acid, D-lactic acid, L-lactic acid, glycolide, glycolic acid, $\epsilon$-caprolactone, $\epsilon$-hydroxy hexonoic acid, $\gamma$-butyrolactone, $\gamma$-hydroxy butyric acid, $\delta$-valerolactone, $\delta$-hydroxy valeric acid, hydroxybutyric acids, malic acid, and copolymers thereof. More preferably, the biodegradable polyester is synthesized from monomers selected from the group consisting of D,L-lactide, D-lactide, L-lactide, D,L-lactic acid, D-lactic acid, L-lactic acid, glycolide, glycolic acid, $\epsilon$-caprolactone, $\epsilon$-hydroxy hexanoic acid, and copolymers thereof. Most preferably, the biodegradable polyester is synthesized from monomers selected from the group consisting of D,L-lactide, D-lactide, L-lactide, D,L-lactic acid, D-lactic acid, L-lactic acid, glycolide, glycolic acid, and copolymers thereof. For purpose of illustration, the A-block copolymers are generally lactide or lactide-co-glycolide moieties. However, unless specifically referred to otherwise, the terms "lactide", "lactate", or "L" shall include all lactic acid derivatives and "glycolide", "glycolate", or "G" shall include all glycolic acid derivatives.

In the hydrophobic polyester A-block of both Components I and II, the molar ratio of lactate content to glycolate content (L:G ratio) is between about 3:1 and about 1:0 preferably between about 1:1 and about 1:0.

Polyethylene glycol (PEG) is sometimes also referred to as poly(ethylene oxide) (PEO) or poly(oxyethylene). The terms can be used interchangeably for the purposes of this invention. The average molecular weight of PEG in Component I is in a range of 900 to 2000, preferably 1000 to 1450. The average molecular weight of PEG in Component II is in a range of 600 to 2000, preferably 900 to 1450. Preferably, Component I has a lower gelation temperature than Component II.

Mixing of two or more types of ABA or BAB triblock polyester polyethylene glycol copolymers can be done by mixing two or more individually synthesized tri-block copolymers, or by synthesizing two or more tri-block copolymers in one reaction vessel. The mixture of copolymers resulting from the above two processes may have the same or different gelation properties. In the latter method, both polymers have polyester A blocks with the same lactide/glycolide ratio, molecular weight and polydispersity.

Additional objects and advantages of this invention will become apparent from the following detailed description of the various embodiments and examples.

BRIEF DESCRIPTION OF THE DRAWINGS

The above and other objects, features and advantages of the invention will become apparent from the following detailed description presented in connection with the accompanying drawings in which.

DETAILED DESCRIPTION OF PREFERRED EMBODIMENTS OF THE INVENTION

This invention provides a reverse gelation system having improved reverse thermal gelation properties which comprises mixtures of various biodegradable polyester/ polyethylene glycol triblock copolymer components. The individual triblock copolymer components can be synthesized separately and then mixed, or be synthesized by polymerization of two or more polyethylene glycol polymers having different molecular weights in one reaction vessel.

As used herein the following terms shall have the assigned meanings:

"Parenteral" shall mean intramuscular, intraperitoneal, intra-abdominal, subcutaneous, and, to the extent feasible, intravenous and intraarterial.

"Gelation temperature" means the temperature at which the biodegradable block copolymer undergoes reverse thermal gelation, i.e. the temperature below which the block copolymer is soluble in water and above which the block copolymer undergoes phase transition to increase in viscosity to form a semi-solid gel. This temperature is also known as the lower critical solution temperature (LCST).

The terms "gelation temperature" and "reverse thermal gelation temperature", "gel/sol temperature" or the like, shall be used interchangeably when referring to the gelation temperature.

"Polymer solution", "aqueous solution", and the like, when used in reference to a biodegradable block copolymer contained in such solution, shall mean a water based solution having such block copolymer mixtures or blends dissolved therein at a functional concentration, and maintained at a temperature below the gelation temperature of the block copolymer mixtures.

"Reverse thermal gelation" is the phenomenon whereby a solution of a block copolymer spontaneously increases in viscosity, and in many instances transforms into a semisolid gel, as the temperature of the solution is increased above the gelation temperature of the copolymer. For the purpose of the invention, the term "gel" includes both the semisolid gel state and the high viscosity state that exists above the gelation temperature. When cooled below the gelation temperature the gel spontaneously reverses to reform the lower viscosity solution. This cycling between the solution and the gel may be repeated indefinitely because the sol/gel transition does not involve any change in the chemical composition of the polymer system. All interactions to create the gel are physical in nature and do not involve the formation or breaking of covalent bonds.

"Drug delivery liquid" or "drug delivery liquid having reverse thermal gelation properties" shall mean a polymer solution that contains a drug and which is suitable for administration to a warm-blooded animal and forms a gelled drug depot when the temperature is raised to or above the gelation temperature of the block copolymer.

"Depot" means a liquid drug delivery system which forms a gel upon the temperature being raised to or above the gelation temperature following administration to a warm-blooded animal.

"Gel" means the semi-solid phase that spontaneously occurs as the temperature of the "polymer solution" or "drug delivery liquid" is raised to or above the gelation temperature of the block copolymer mixture.

"Aqueous polymer composition" means either a drug delivery liquid or a gel comprised of the water phase, having uniformly contained therein, a drug and the mixture of biodegradable block copolymers. At temperatures below the gelation temperature the mixture of block copolymers may be soluble in the water phase and the composition will be a solution. At temperatures at or above the gelation temperature, the mixture of block copolymers will solidify to form a gel with the water phase, and the composition will be a gel or semi-solid.

"Biodegradable" means that the block copolymer components can chemically break down or degrade within the body to form nontoxic components. The rate of degradation can be the same or different from the rate of drug release.

"Drug" shall mean any organic or inorganic compound or substance having bioactivity and adapted or used for therapeutic purposes. Proteins, hormones, anti-cancer agents, oligonucleotides, DNA, RNA and gene therapies are included under the broader definition of "drug".

"Peptide," "polypeptide," "oligopeptide" and "protein" shall be used interchangeably when referring to peptide or protein drugs and shall not be limited as to any particular molecular weight, peptide sequence or length, field of bioactivity or therapeutic use, unless specifically stated.

"Poly(lactide-co-glycolide)" or "PLG" shall mean a copolymer derived from the condensation copolymerization of lactic acid and glycolic acid, or, by the ring opening polymerization of a-hydroxy acid precursors, such as lactide or glycolide. The terms "lactide, " "lactate," "glycolide" and "glycolate" are used interchangeably as noted above.

"Polylactide" or "PLA" shall mean a polymer derived from the condensation of lactic acid or by the ring opening polymerization of lactide. The terms "lactide" and "lactate" are used interchangeably.

"Biodegradable polyesters" refers to any biodegradable polyesters, which are preferably synthesized from monomers selected from the group consisting of D,L-lactide, D-lactide, L-lactide), D,L-lactic acid, D-lactic acid, L-lactic acid, glycolide, glycolic acid, ε-caprolactone, ε-hydroxy hexanoic acid, γ-butyrolactone, γ-hydroxy butyric acid, δ-valerolactone, δ-hydroxy valeric acid, hydroxybutyric acids, malic acid, and copolymers thereof.

"Reverse thermal gel" or "reverse thermal gelation system" refers to all biodegradable triblock polyester PEG copolymers having reverse thermal gelation properties. A detailed description of reverse gelation systems has been disclosed and referenced above.

"Gel mixture" or "mixture of triblock copolymers" refers to a reverse gelation system comprising two or more ABA or BAB triblock polyester-polyethylene glycol copolymer components. The mixture can be made either by simply mixing two or more individually synthesized triblock copolymer components, or by synthesizing two or more types of copolymer systems in one synthesizing vessel. The mixture prepared by the above two processes may have the same or different gelation properties and gel qualities.

The present invention is based on the discovery that mixtures of two or more triblock polyester PEG copolymers will provide for a copolymer mixture having improved reverse gelation properties such as flexible gelation temperature, gel strength, and yet still maintain desirable gel qualities. In addition, such drug delivery systems have the ability in order to modulate drug release, and matrix erosion. Thus, the combination of two or more individual triblock copolymers substantially increases design flexibility of the drug delivery system to fit individual needs.

In a preferred embodiment, as illustrated in Table 1, the individual component I triblock copolymers of this invention comprise tri-block copolymers of a biodegradable polyester and polyethylene glycol (PEG) having an average molecular weight of between about 2500 Daltons and about 8000 Daltons, preferably 3000 Daltons to 6500 Daltons, and consists of a biodegradable polyester block and a polyethylene glycol (PEG) block in a ratio by weight of 1.3 to 3.0, and preferably between 1.8 to 2.6. The component II triblock copolymers have an average molecular weight of about 800 Daltons to about 7200 Daltons, preferably 1500 Daltons to 6000 Daltons, and consist of a biodegradable polyester and a polyethylene glycol (PEG) in a ratio by weight of 0.37 to 2.6, preferably between 0.54 and 2.5. The biodegradable, hydrophobic A-block polymer may be comprised of a polyester synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxy hexonoic acid, γ-butyrolactone, γ-hydroxy butyric acid, δ-valerolactone, δ-hydroxy valeric acid, hydroxybutyric acids, malic acid, and copolymers thereof.

TABLE 1

|   | Range | Preferred Range |
|---|---|---|
| Component I: | | |
| B-polymer block MW | 900 to 2000 Daltons | 1000 to 1450 Daltons |
| A-block/B-block weight ratio | 1.3 to 3.0 | 1.8 to 2.6 |
| L:G mole ratio in A-block | 3:1 to 1:0 | 1:8 to 1:0 |
| Tri-block copolymer MW | 2500 to 8000 Daltons | 3000 to 6500 Daltons |
| Component II: | | |
| B-polymer block MW | 600 to 2000 Daltons | 900 to 1450 Daltons |
| A-block/B-block weight ratio | 0.37 to 2.6 | 0.54 to 2.6 |
| L:G mole ratio in A-block | 3:1 to 1:0 | 1:1 to 1:0 |
| Tri-block copolymer MW | 800 to 7200 Daltons | 1500 to 6000 Daltons |

The triblock copolymer components of the present invention may be synthesized by ring opening polymerization or by condensation polymerization according to reaction schemes disclosed in U.S. Pat. Nos. 5,702,717 and 6,006,573, hereby fully incorporated by reference. For example, the PEG blocks may be coupled to the biodegradable polyester by ester or urethane links and the like. Condensation polymerization and ring opening polymerization procedures may be utilized as may the coupling of a monofunctional hydrophilic B block to either end of a difunctional hydrophobic A block in the presence of coupling agents, such as isocyanates. Furthermore, coupling reactions may follow activation of functional groups with activating agents such as carbonyl diimidazole, succinic anhydride, N-hydroxy succinimide and p-nitrophenyl chloroformate and the like.

The hydrophilic B-block of the present invention is selected from appropriate molecular weights of PEG. PEG was chosen as the hydrophilic, water-soluble block because of its unique biocompatibility, nontoxicity, hydrophilicity, solubilization properties, and rapid clearance from a patient's body.

The hydrophobic polyester blocks are selected because of their biodegradable, biocompatible, and solubilizing properties. The in vitro and in vivo degradation of these hydrophobic, biodegradable polyester blocks is well understood and the degradation products are naturally occurring compounds that are readily metabolized and/or eliminated by the patient's body.

Surprisingly, by blending or mixing two or more polyester PEG triblock copolymers, either as individually synthesized copolymers or synthesized together in one reaction vessel, the resulting triblock copolymer mixture maintains a combination of desirable water solubility and reverse thermal gelation properties. It is unexpected that, by selecting suitable triblock copolymer components having different gelation temperatures and then mixing them in proper ratios, the resulting triblock copolymer mixtures have a reverse gelation temperatures that varies between of 0 and 50° C., variable erosion duration from one day to ten weeks, and yet maintains desirable gel qualities. Aside from optimizing the gelation properties and gel qualities of each copolymer component, mixing two or more biodegradable triblock copolymer components offers significantly increased flexibility in designing drug delivery systems as necessary to fit individual needs.

The concentration at which the block copolymers are soluble at temperatures below the gelation temperature may be considered as the functional concentration. Generally speaking, total block copolymer concentrations of as low as 3% and up to about 50% by weight can be used and still be functional. However, concentrations in the range of about 5 to 40% are preferred and concentrations in the range of about 10 to 30% by weight are most preferred. In order to obtain a viable gel phase transition with the copolymer, a certain minimum concentration, e.g. 3% by weight, is required. At the lower functional concentration ranges, the phase transition may result in the formation of a weak gel. At higher concentrations, a stronger gel network is formed.

A drug loaded triblock copolymer mixture having improved reverse gelation properties may be prepared in the same manner as the previously referenced individual triblock copolymer drug deliver systems are prepared. An aqueous solution of the triblock copolymer mixture of the present invention, at a temperature below the gelation temperature, forms a drug delivery liquid where the drug may be either partially or completely dissolved. When the drug is partially dissolved, or when the drug is essentially insoluble, the drug exists in a colloidal state, such as a suspension or emulsion. This drug delivery liquid is then administered parenterally, topically, transdermally, transmucosally, inhaled, or inserted into a cavity such as by ocular, vaginal, transurethral, rectal, nasal, oral, buccal, pulmonary or aural administration, whereupon it will undergo reversible thermal gelation since body temperature will be above the gelation temperature.

Due to the biocompatibility, the biodegradability and the pliability of the triblock copolymers of the present invention, this mixture of the triblock copolymer components will cause minimal toxicity and mechanical irritation to the surrounding tissues. The drug release, gel strength, gelation temperature and degradation rate can be controlled by the proper design and selection of the various copolymer components, namely, through proper selection of individual copolymer components and ratios of individual copolymer components to prepare the mixture. The mixture will present modified and/or combinations of the gelation properties and gel qualities of the individual copolymer components. Particularly, mixtures of various types of triblock copolymer components in the proper ratios provides for a wide range of reverse gelation temperatures, such as from 0° C. to 50° C. With the availability of a gelation temperature close to room temperature but below body temperature, provided by the copolymer mixture of the present invention, the handling procedure is simplified and the cost reduced. It also decreases the risk of premature gelation during application, i.e. gelation in the syringe. More significantly, unlike other means of modifying gelation temperature, the copolymer mixtures of this invention maintain the desirable gel qualities of the individual copolymer components and yet provides for more flexibility in designing a more specific drug delivery system to fit individual needs. Drug release is also controllable through adjustment of the concentration of the mixture in the drug delivery liquid.

A dosage form comprised of a solution of a mixture of two or more copolymer components that contains either dissolved drug, or drug as a suspension or emulsion, is administered to the body of a patient. Due to the reverse thermal gelation properties of the block copolymer mixtures, this formulation then spontaneously gels to form a drug depot as the temperature of the formulation rises to the gelation temperature. The only limitation as to how much drug can be loaded into the formulation is one of functionality, namely, the drug load may be increased until the thermal gelation properties of the copolymer mixtures are adversely affected to an unacceptable degree, or until the properties of the formulation are adversely affected to such a degree as to make administration of the formulation unacceptably difficult. Generally speaking, it is anticipated that in most instances the drug will make up between about 0.0001 to 30% by weight of the formulation with ranges of between about 0.0001 to 20% being referred. These ranges of drug loading are not limiting to the invention. Provided functionality is maintained, drug loadings outside of these ranges may also fall within the scope of the invention.

A distinct advantage to the compositions of the subject of this invention lies in the ability of the triblock copolymer mixtures to increase the solubility of many drug substances. The combination of the hydrophobic polyester block(s) and hydrophilic block(s) PEG of the copolymer components of the mixture renders the block copolymer component surface-active in nature. In that regard, it functions much as a soap or surfactant in having both hydrophilic and hydrophobia properties. This is particularly advantageous for the solubilization of hydrophobic or poorly water soluble drugs, such as cyclosporin and paclitaxel. What is surprising is the degree of drug solubilization of most, if not all, drugs since the major content of the block copolymer is the hydrophobic polyester block content. However, as already discussed, even though the hydrophobic polymer block(s) are the major content, the block copolymer is water soluble and it has been found that there is an additional increase in drug solubility when combined in an aqueous phase of the block copolymer.

Another advantage of the composition of the present invention lies in the ability of the triblock copolymer mixture to increase the chemical stability of many drug substances. Various mechanisms for degradation of drugs, that lead to a drug's chemical degradation, are retarded when the drug is in the presence of the block copolymer mixture. For example, paclitaxel and cyclosporin A are substantially stabilized in the aqueous polymer composition of the present invention relative to certain aqueous solutions of these same drugs in the presence of organic co-solvents. This stabilization effect on paclitaxel and cyclosporin A is but illustrative of the effect that would be achieved with many other drug substances.

In certain situations the drug loaded polymer may be administered in the gel state instead of as a solution. The gelation may be the result of raising the temperature of a drug laden polymer solution to above the gelation temperature of the polymer prior to administration, or may be caused by raising the concentration of the polymer in the solution to above the saturation concentration at the temperature of administration, or it may be caused by additives to the polymer solution which cause the solution to gel. In either event, the gel thus formed may be administered parenterally, topically, transdermally, transmucosally, inhaled or inserted into a cavity such as by ocular, vaginal, buccal, transurethral, rectal, nasal, oral, pulmonary or aural administration.

This invention is applicable to bioactive agents and drugs of all types including oligonucleotides, hormones, anticancer-agents. It offers an unusually effective way to deliver polypeptides and proteins. Many labile peptide and protein drugs are amenable to formulation into the block copolymers of the invention and can benefit from the reverse thermal gelation process described herein. While not specifically limited to the following, examples of pharmaceutically useful polypeptides and proteins may be selected from the group consisting of erythropoietin, oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, growth hormone (human, porcine, bovine, etc.), growth hormone releasing factor, insulin, somatostatin, glucagon, interleukin-2 (IL-2), interferon-α, β, or γ, gastrin, tetragastrin, pentagastrin, urogastrone, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), heparinase, bone morphogenic protein (BMP), hANP, glucagon-like peptide (GLP-1), interleukin-11 (IL-11), renin, bradykinin, bacitracins, polymyxins, colistins, tyrocidine, gramicidins, cyclosporins and synthetic analogues, modifications and pharmacologically active fragments thereof, enzymes, cytokines, antibodies and vaccines.

The only limitation to the polypeptide or protein drug which may be utilized is one of functionality. In some instances, the functionality or physical stability of polypeptides and proteins can also be increased by the addition of various additives to aqueous solutions or suspensions of the polypeptide or protein drug. Additives, such as polyols (including sugars), amino acids, surfactants, polymers, other proteins and certain salts may be used. These additives can readily be incorporated into the triblock copolymer mixtures, which will then undergo the reverse thermal gelation process of the present invention.

Developments in protein engineering may provide for the possibility of increasing the stability of peptides or proteins. While such resulting engineered or modified proteins may be regarded as new entities to regulatory agents, those modifications do not alter their suitability for use in the present invention. One of the typical examples of modification is PEGylation, where the stability of the polypeptide drugs can be significantly improved by covalently conjugating water-soluble polymers, such as polyethylene glycol, with the polypeptide. Another example is modification of the amino acid sequence by addition, deletion or substitution of one or more amino acid residues, at terminal and/or internal locations. Any such modified polypeptide or protein with its improved stability or efficacy is within the scope of the present invention.

In addition to peptide or protein based drugs, other drugs from all therapeutic and medically useful categories may be utilized. These drugs are described in such well-known literature references as the Merck Index, the Physicians Desk Reference, and The Pharmacological Basis of Therapeutics. A brief listing of specific agents is provided for illustration purposes only, and shall not be deemed as limiting: anti-cancer agents such as mitomycin, bleomycin, BCNU, carboplatin, doxorubicin, daunorubicin, methotrexate, paclitaxel, taxotere, actinomycin D and camptothecin; antipsychotics such as olanzapine and ziprasidone; antibacterials such as cefoxitin; anthelmintics such as ivermectin; antivirals such as acyclovir; immunosuppressants such as cyclosporin A (cyclic polypeptide-type agent), steroids, and prostaglandins.

The following are examples that illustrate preferred embodiments of the invention, but are intended as being representative only.

EXAMPLES

Example 1

Synthesis of PLG-PEG-PLG Tri-block Copolymers

The synthesis process utilized in this example is generally disclosed in U.S. Pat. No. 6,004,573 and is hereby incorporated by reference. Poly(ethylene glycol) (PEG-1000; 29.4 gram) was weighed and-transferred into a 250-mL 3-neck round bottom flask. The flask was attached to a vacuum line (1–2 torr) and immersed in an oil bath. Residual water was removed by raising the bath temperature to 155° C. for 3 hours. The flask was raised and allowed to cool to about 80° C. D,L-lactide (55.65 gram) and glycolide (14.95 gram) were weighed and added to the flask. The headspace of the flask was replaced by dry nitrogen and heating resumed (130° C.) until the lactide and glycolide were melted. Polymerization was initiated by addition of 0.02 g of stannous octoate dropwise over a one minute time period. The reaction mixture was heated at 155° C. for an additional eight hours. Monomers were removed by vacuum (1–2 torr) for ca. 2 hours and the residue was dissolved in cold water (4° C.). Water soluble oligomers and monomers were removed by precipitation of the desired polymer in hot water (80° C.). Water was removed by freeze-drying. Molecular weight of the resulting triblock copolymer was determined by gel permeation chromotograph and to be 4080 Daltons. A 23% by weight aqueous solution of the polymer was soluble in-cold water and gelled at 13.1° C. as the temperature was raised.

Example 2

This example was done by following the procedure described in Example 1 but using 37.74 gram of poly (ethylene glycol) (PEG 1450), 49.1 gram of D,L-lactide and 13.18 gram of glycolide in the synthesis. Molecular weight of the resulting triblock copolymer was determined by gel permeation chromatograph to be 4610 Daltons. A 23% by weight aqueous solution of the synthesized polymer was soluble in cold water and gelled at 42.3° C.

Example 3

Figure 1:
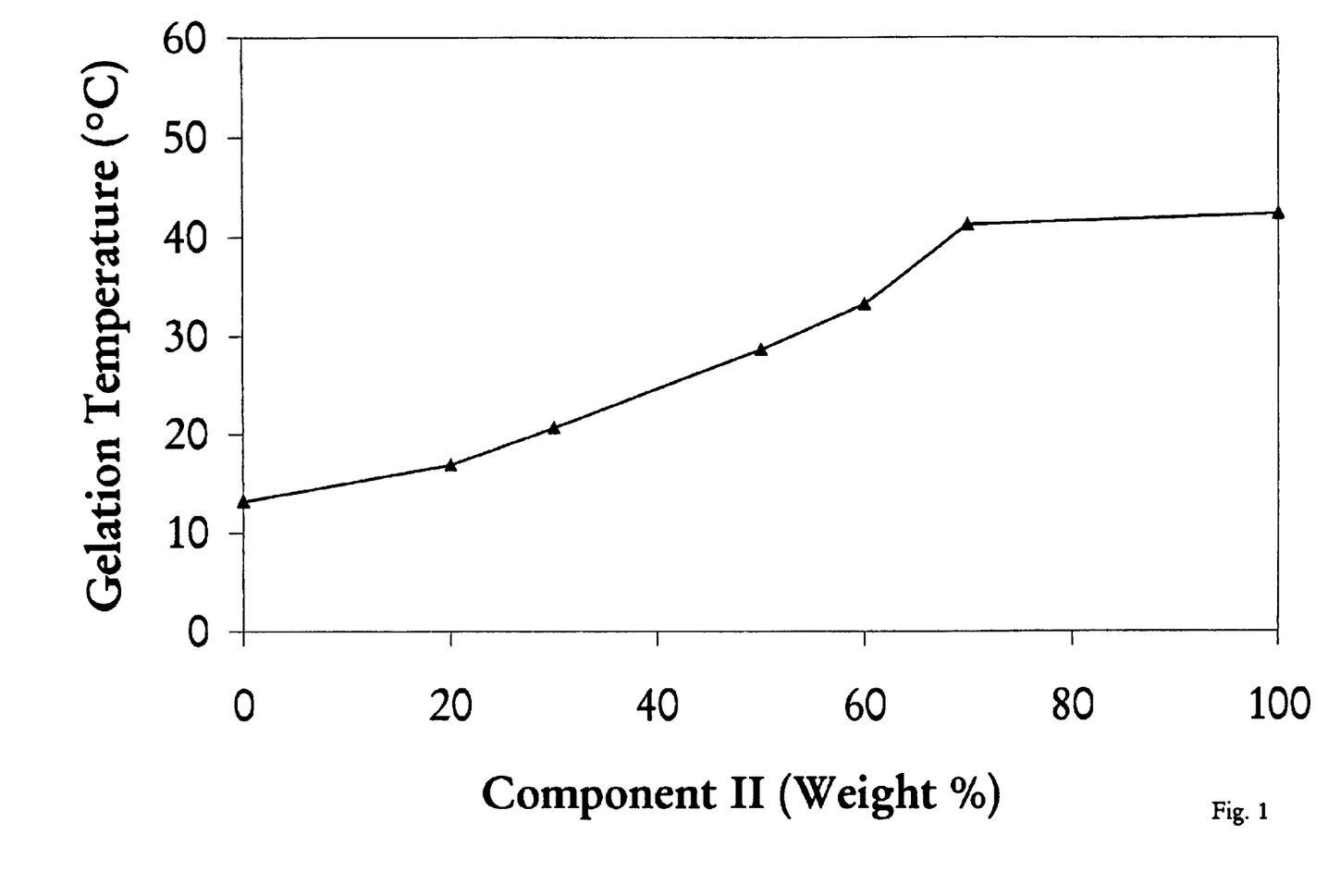
FIG. 1 Corresponding to Example 3, illustrates the gelation temperature of a solution (23% w/w) containing a mixture of Components I and II as a function of percentage by weight of Component II in the mixture.

This example illustrates a method for making a triblock copolymer mixtures with various selectable reverse thermal gelation temperatures by mixing two pre-made individual triblock copolymer solutions. Tri-block copolymers prepared by the method described in Example 1 (Component I) and Example 2(Component II) were dissolved in water to form 23% by weight solutions. These two solutions were mixed and gelation temperatures were measured. As illustrated in FIG. 1, the gelation temperature of the mixture of Component I and Component II triblock copolymers rises from about 13° C. (100% Component I) when the content of Component II in the mixture increases, up to 42° C. when the content of Component II triblock copolymer reaches 100%.

Example 4

This example illustrates a method of preparing a triblock copolymer mixture, having reverse thermal gelation properties, by simultaneously synthesizing two different triblock copolymer components in one reaction vessel.

PEG 1450 (22.74 gram) and PEG 1000 (9.11 gram) were weighed and transferred into a 250-mL 3-neck round bottom flask. The flask was attached to a vacuum line (1–2 torr) and immersed in an oil bath. Residual water was removed by raising the bath temperature to 155° C. for 3 hours. Then, the flask was raised and allowed to cool to ca. 80° C. D,L-lactide (53.73 gram) and glycolide (14.1 gram) were weighed and added to the flask. The headspace of the flask was replaced by dry nitrogen and heating resumed (130° C.) until the lactide and glycolide were completely melted. Polymerization was initiated by the addition of 0.02 g of stannous octoate (dropwise over 1 minute). The reaction mixture was heated at 155° C. for an additional eight hours. Monomers were removed by vacuum distillation (1–2 torr) for about 2 hours and the residue was dissolved in cold water (4° C.). Water soluble oligomers and monomers were removed by precipitation of the desired polymer in hot water (80° C.). Water was removed by freeze-drying. Molecular weight of the resulting triblock copolymer was determined by gel permeation chromatograph and to be 4910 Daltons. The gelling temperature of the polymer solution (23% by weight) was 22.1° C.

Example 5

This example illustrates a mixture of a triblock copolymer solution (23% by weight in water) having an extremely high viscosity and a triblock copolymer solution (23% by weight in water) having a low viscosity.

Figure 2:
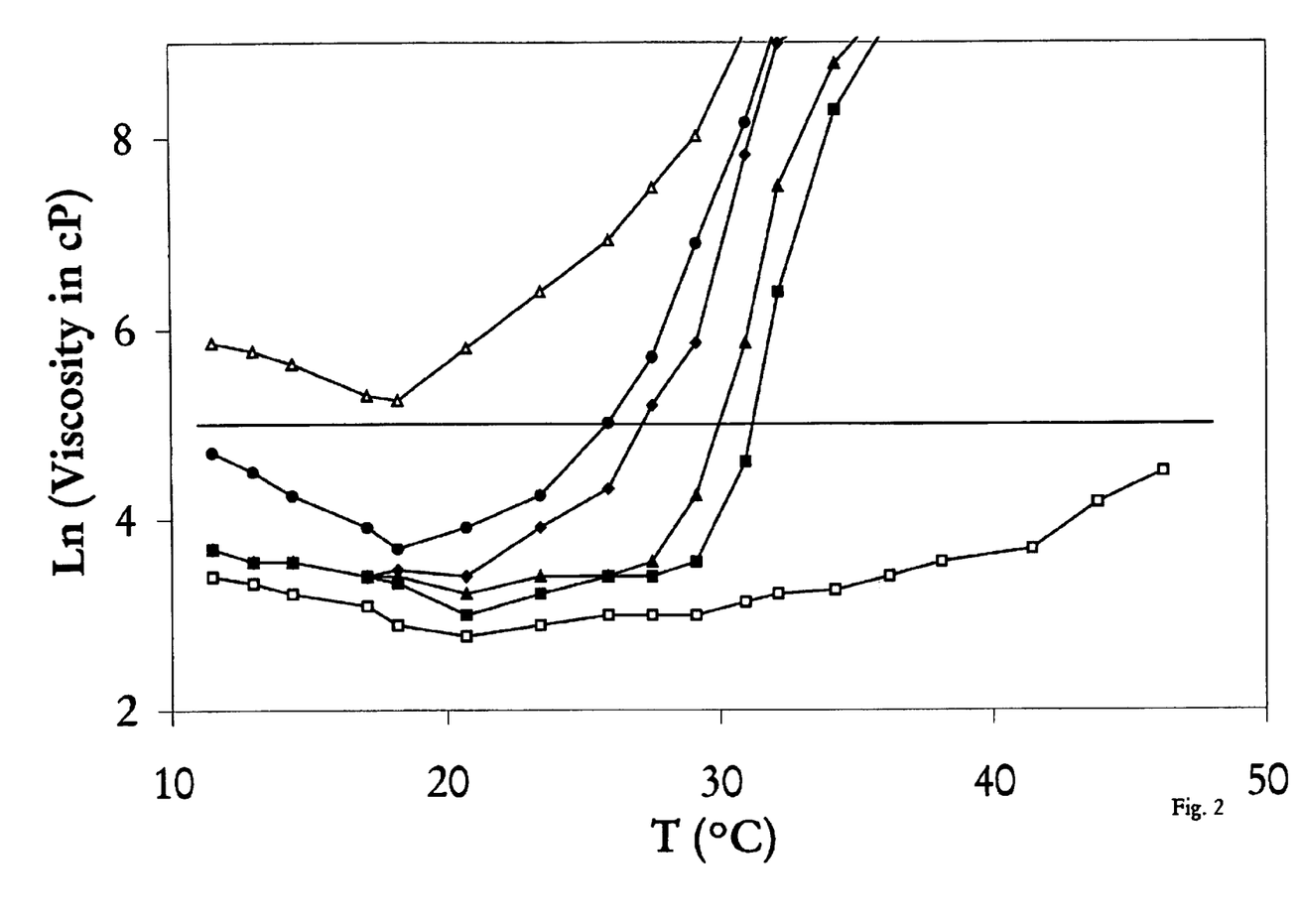
FIG. 2 Corresponding to Example 5, illustrates the gelation temperature of a mixture of a nearly water-insoluble copolymer (Component I), and a low molecular weight water-soluble copolymer (Component II) at varying concentrations.

A Component I tri-block copolymer was prepared according to Example 2 except that PEG1450 was used as B-polymer block, the weight ratio of A-polymer block to B-polymer block was 2.6:1, and the lactide/glycolide mole ratio (L/G) in the A-polymer block was 3:1. A 23% by weigh aqueous solution of this Component I triblock copolymer was very viscous, with a honey-like consistency. Similarly, a Component II tri-block copolymer was prepared according to Example 2 except that PEG900 was used as B-polymer block, the weight ratio of A-polymer block B-polymer block was 0.8:1, and the lactide/glycolide mole ratio (L/G) in the A-polymer block was 3:1. An aqueous solution of the Component II tri-block copolymer had a low viscosity and did not form a gel between 0–100° C. at any concentration. Five mixtures of Components I and Components II triblock copolymers were prepared with total polymer content fixed at 23% by weight. The weight percent of Component II triblock copolymer in the copolymer mixture was between 10 to 30%. The viscosity profiles and gelation temperatures of the mixtures of Component I and Component II triblock copolymers are shown in FIG. 2. In FIG. 2, various concentrations of the Component II triblock copolymer in the mixture are represented by the following symbols: 10% (Δ), 15% (●), 20% (♦), 25% (▲), 30% (■) and 100% (□). The solid line represents the viscosity at which these copolymer mixture solutions enter the gel phase at the gelation temperature indicated.

These data show that by mixing a low viscosity tri-block copolymer solution and a high viscosity triblock copolymer solution, the resulting mixture has a viscosity low enough to easily pass through a 26-gauge hypodermic needle, and yet have a reverse thermal gelation temperature of between 26 to 32° C.

Example 6

Drug Release

This example illustrates the drug release profile from triblock copolymer mixture solutions of the present invention using zinc insulin as a model protein drug.

A Component I tri-block copolymer prepared in Example 1 was dissolved in 10 mM HEPES buffer (pH 7.4) to form a 20% solution. Similarly, Component II solution (20%) 10 mM HEPES buffer (pH 7.4) was prepared by dissolving a Component II tri-block copolymer prepared as described in Example 1 except that PEG1450 was used as B-polymer block, the weight ratio of A A polymer block/B-polymer block was 2.15:1 and the lactide/glycolide (L/G) mole ratio of A-polymer block was 4:1. Two solutions of these tri-block copolymers mixtures into 10 mM HEPES buffer (pH 7.4, containing 50 mM EDTA) were also prepared by mixing Component I tri-block copolymer/Component II tri-block copolymer by weight ratios of 1:1 and 1:3 respectively. The final copolymer concentration in these solutions were 20% by weight.

Figure 3:
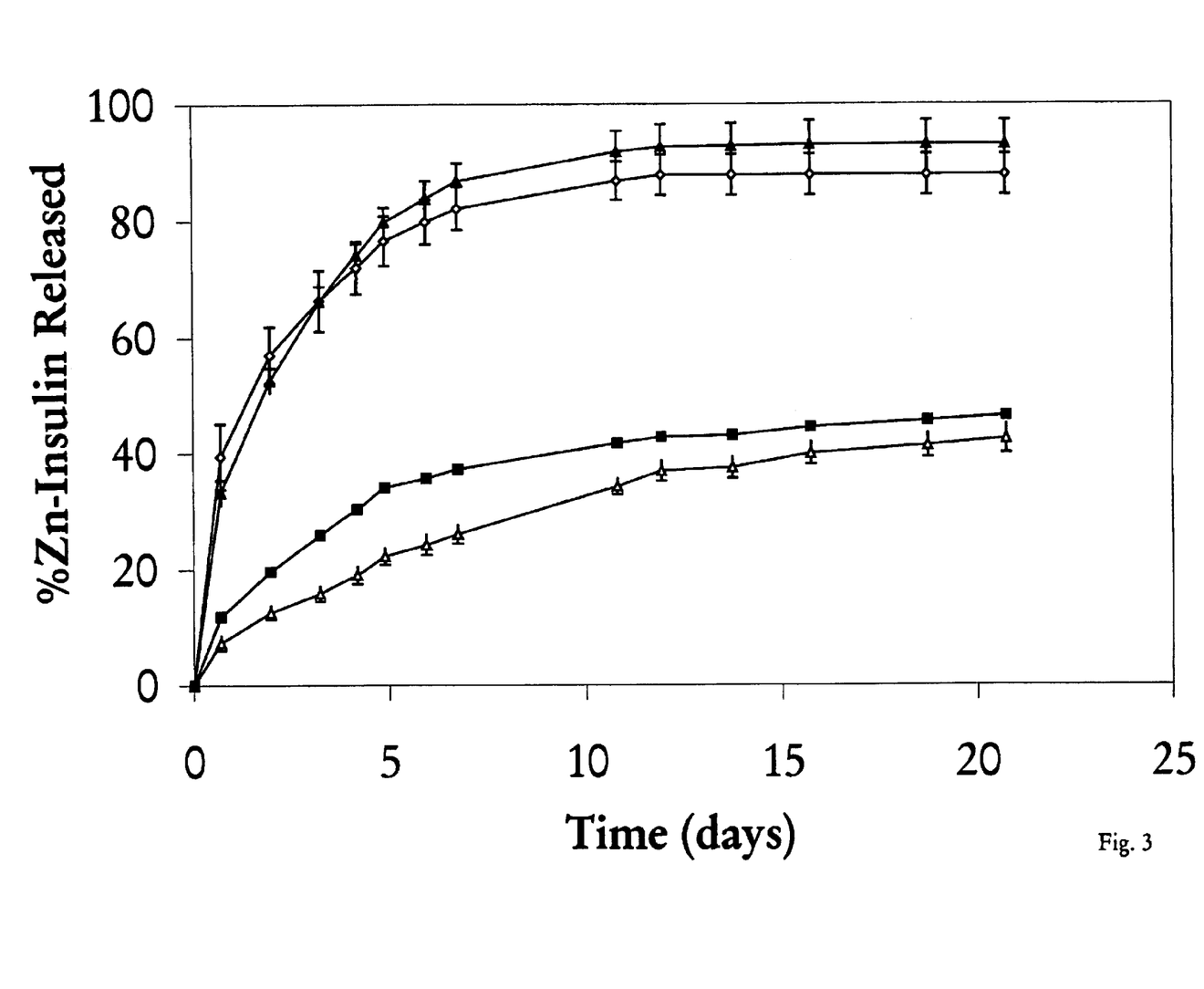
FIG. 3 Corresponding to, Example 6, illustrates the dissolution of zinc-insulin from a gel composed of mixtures of Component I triblock copolymers and Component II triblock copolymers in varying ratios.

Zinc insulin (7.5 mg) was suspended in 1.58 mL of HEPES buffer. Aliquots (20-μL) of the suspension were added to vials so that each vial had 950 μg of the zinc insulin. To each vial was further added 100 μL of one of the triblock copolymer solutions prepared as describe above. The contents of the vials were thoroughly mixed, and placed in an oven (37° C.) to cause gelling before 1 mL of pre-warmed (37° C.) dissolution medium (10 mM HEPES buffer (pH 7.4) containing 50 mM EDTA) was added. The vials were placed in a 37° C. oven and the dissolution medium was replaced periodically. Insulin in the dissolution medium was analyzed by HPLC. The results are presented in FIG. 3 with the following symbols representing various triblock copolymer solutions: 100% Component I (Δ), 100% Component II (◊), 1:3 w/w mixture of Component I and Component II (■), and 1:1 w/w mixture of Component I and Component II (▲).

These data show that the release rate of zinc-insulin could be modulated to fit individual needs by mixing two different tri-block copolymer solutions, which provide a significant advancement in the art.

Example 7

Figure 4:
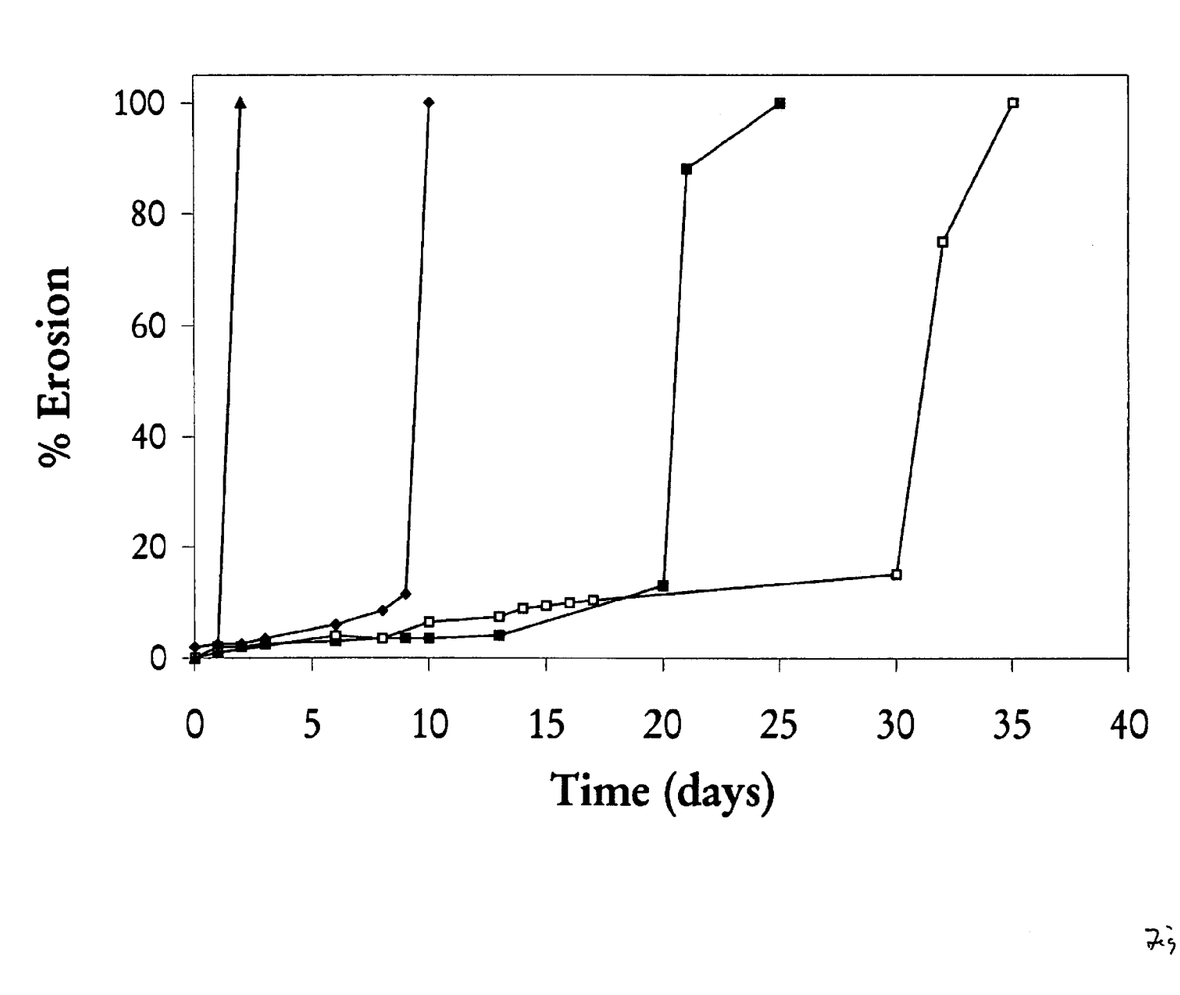
FIG. 4 Corresponding to Example 7, illustrates the erosion (37° C.) of gels prepared by mixing two triblock copolymers with various weight ratios of Component I and Component II.

Modulation of the Erosion of Triblock Copolymer Reverse Thermal Gelation Systems by Mixing Two Copolymer Solutions Component I triblock copolymer prepared in the Example 1 and Component II triblock copolymer prepared in the Example 2 were dissolved individually in water to form 23% by weight solutions. The Component II triblock copolymer solution had a gel temperature of 42.3° C. and therefore no gel was observable at 37° C. Three mixtures of above prepared Component I triblock copolymer solution and Component II triblock copolymer solution were prepared at ratios of 3:1, 1:1 and 1:3 respectively. 3 mL aliquots of these three solution mixtures were placed in 20 mL scintillation vials. After the gel was set (37° C., 1 minute), to each vial was added 5 mL of water (37° C.). Periodically, the water layer was collected and replaced. Water was removed by lyophilization and the amount of polymer eroded was measured gravimetrically. The results presented in FIG. 4, with the following symbols representing various weight ratios of Component I and Component II in the mixtures: 1:0 (□), 3:1 (■), 1:1 (♦), and 1:3 (▲). The results clearly show that the duration of the gel phase could be modulated by mixing two polymer solutions of different gelation temperatures.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

We claim:

1. A biodegradable polymeric system possessing reverse thermal gelation properties comprising a mixture of at least a Component I triblock copolymer and a Component II triblock copolymer, said triblock copolymers comprising biodegradable polyester A-polymer blocks and polyethylene glycol B-polymer blocks, wherein the B-polymer block of said Component I triblock copolymer has an average molecular weight of 900 to 2000 Daltons and the B-polymer block of said Component II triblock copolymer has an average molecular weight of 600 to 2000 Daltons, and wherein said Component I triblock copolymer has an average molecular weight of between 2500 to 8000 Daltons and said component II triblock copolymer has an average molecular weight of between 800–7200 Daltons, and wherein said biodegradable polymeric system is water soluble and contains 51 to 83% by weight of hydrophobic A polymer blocks and 17 to 49% by weight of hydrophilic B polymer blocks wherein an aqueous solution of said Component I triblock copolymer has a lower gelation temperature than an aqueous solution of said Component II triblock copolymer.

2. The biodegradable polymeric system according to claim 1 wherein the biodegradable polyester A-polymer block is synthesized from monomers selected from the group consisting of D,L-lactide, D-lactide, L-lactide, D,L-lactic acid, D-lactic acid, L-lactic acid, glycolide, glycolic acid, $\epsilon$-caprolactone, $\epsilon$-hydroxyhexanoic acid, $\gamma$-butyrolactone, $\gamma$-hydroxybutyric acid, $\delta$-valerolactone, $\delta$-hydroxyvaleric acid, hydroxybutyric acids, malic acid, and copolymers thereof.

3. The biodegradable polymeric system according to claim 1 wherein Component I and Component II triblock copolymers are selected from the group consisting of ABA and BAB type copolymers and mixtures thereof.

4. The biodegradable polymeric system according to claim 3 wherein the Component I and Component II triblock copolymers are each of the BAB type.

5. The biodegradable polymeric system according to claim 3 wherein the Component I and Component II triblock copolymers are each of the ABA type.

6. The biodegradable polymeric system according to claim 3 wherein the Component I triblock copolymer is an ABA type and the Component II triblock copolymer is a BAB type.

7. The biodegradable polymeric system according to claim 3 wherein the Component I triblock copolymer is a BAB type and the Component II triblock copolymer is an ABA type.

8. The biodegradable polymeric system according to claim 2 wherein the A-polymer block is a biodegradable polyester synthesized from monomers selected from the group consisting of D,L-lactide, D-lactide, L-lactide, D,L-lactic acid, D-lactic acid, L-lactic acid, glycolide, glycolic acid, $\epsilon$-caprolactone, $\epsilon$-hydroxyhexanoic acid, and copolymers thereof.

9. The biodegradable polymeric system according to claim 8 wherein the biodegradable A-polymer block is poly(D,L-lactide-co-glycolide) (PLG) synthesized from monomers selected from the group consisting of D,L-lactide, D-lactide, L-lactide, D,L-lactic acid, D-lactic acid, L-lactic acid, glycolide, glycolic acid, and copolymers thereof.

10. The biodegradable polymeric system according to claim 9 wherein the A-polymer block of each Component I and Component II tri-block copolymer has a mole ratio of lactide to glycolide in a range of between 3:1 to 1:0.

11. The biodegradable polymeric system according to claim 10 wherein the A-polymer block of each Component I and Component II tri-block copolymer has a mole ratio of lactide to glycolide in a range of between 1:1 to 1:0.

12. The biodegradable polymeric system according to claim 9 wherein the Component I triblock copolymer has A-polymer block/B-polymer block weight ratio between 1.3 to 3.0 and the Component II triblock copolymer has A-polymer block/B-polymer block weight ratio between 0.37 to 2.6.

* * * * *